(12) United States Patent
Budill et al.

(10) Patent No.: US 11,464,588 B1
(45) Date of Patent: Oct. 11, 2022

(54) SYSTEMS AND METHODS FOR AUTOMATED CONTROL OF MEDICAL INSTRUMENTS USING ARTIFICIAL INTELLIGENCE

(71) Applicant: BH2 INNOVATIONS INC., Newbury Park, CA (US)

(72) Inventors: Stephen J. Budill, San Francisco, CA (US); Michael S. Humason, Newbury Park, CA (US); Salmaan Hameed, San Jose, CA (US)

(73) Assignee: BH2 INNOVATIONS INC., Newbury Park, CA (US)

( * ) Notice: Subject to any disclaimer, the term of this patent is extended or adjusted under 35 U.S.C. 154(b) by 0 days.

(21) Appl. No.: 17/721,181

(22) Filed: Apr. 14, 2022

Related U.S. Application Data

(63) Continuation of application No. 17/534,680, filed on Nov. 24, 2021, now Pat. No. 11,311,346.

(51) Int. Cl.
| | |
|---|---|
| *G06K 9/00* | (2022.01) |
| *A61B 34/32* | (2016.01) |
| *G06T 7/00* | (2017.01) |

(52) U.S. Cl.
CPC ........... *A61B 34/32* (2016.02); *G06T 7/0014* (2013.01); *G06T 2207/10048* (2013.01); *G06T 2207/20076* (2013.01); *G06T 2207/20081* (2013.01); *G06T 2207/20084* (2013.01)

(58) Field of Classification Search
CPC ............... A61B 34/32; G06T 7/0014; G06T 2207/10048; G06T 2207/20076; G06T 2207/20081; G06T 2207/20084

USPC ........................................................ 600/130
See application file for complete search history.

(56) References Cited

U.S. PATENT DOCUMENTS

| | | | | |
|---|---|---|---|---|
| 2001/0036245 | A1* | 11/2001 | Kienzle, III | A61B 90/36 378/4 |
| 2008/0004633 | A1* | 1/2008 | Arata | A61B 34/10 606/130 |
| 2009/0099867 | A1* | 4/2009 | Newman | G16H 40/40 705/2 |
| 2010/0168562 | A1* | 7/2010 | Zhao | A61B 34/30 600/426 |
| 2014/0350614 | A1* | 11/2014 | Frey | A61B 34/10 606/86 R |

(Continued)

*Primary Examiner* — Van D Huynh
(74) *Attorney, Agent, or Firm* — Ansari Katiraei LLP; Arman Katiraei; Sadiq Ansari

(57) ABSTRACT

Disclosed is a system and method for assembling instrument sets that include correct instruments with one or more verified states for different procedures. The system may receive a request for a particular instrument, and may determine instrument states defined for the particular instrument or a procedure involving the particular instrument. The system may scan a first instrument using one or more sensors, may verify that the first instrument matches a make, model, or type of the particular instrument based on the scanning data, and may classify the first instrument states with at least a threshold probability based on the scanning data matching characteristics from a probabilistic model. The system may control the distribution of the first instrument to a first destination or a second destination based on whether or not the first instrument states satisfy the instrument states defined for the particular instrument or the procedure.

20 Claims, 8 Drawing Sheets

(56) References Cited

U.S. PATENT DOCUMENTS

| | | | |
|---|---|---|---|
| 2016/0015471 A1* | 1/2016 | Piron | A61B 1/00059 |
| | | | 600/424 |
| 2017/0252472 A1* | 9/2017 | Dang | G16H 40/40 |
| 2018/0199996 A1* | 7/2018 | Hogan | A61B 34/10 |
| 2019/0051408 A1* | 2/2019 | Hanajima | A61B 34/25 |
| 2019/0099180 A1* | 4/2019 | Leimbach | G16H 40/63 |
| 2020/0005936 A1* | 1/2020 | Hanajima | G16H 40/20 |
| 2020/0043605 A1* | 2/2020 | Hanajima | A61B 90/90 |
| 2020/0375433 A1* | 12/2020 | Polosky | A61B 1/00029 |
| 2021/0212784 A1* | 7/2021 | Ramadorai | A61B 34/37 |

\* cited by examiner

SYSTEMS AND METHODS FOR AUTOMATED CONTROL OF MEDICAL INSTRUMENTS USING ARTIFICIAL INTELLIGENCE

CLAIM OF BENEFIT TO RELATED APPLICATIONS

This application is a continuation of U.S. nonprovisional application Ser. No. 17/534,680 entitled "SYSTEMS AND METHODS FOR AUTOMATED CONTROL OF MEDICAL INSTRUMENTS USING ARTIFICIAL INTELLIGENCE", filed June Nov. 24, 2021. The contents of application Ser. No. 17/534,680 are hereby incorporated by reference.

BACKGROUND

Successful medical procedures may depend on well-maintained and properly selected medical instruments. A surgeon may desire a specific type of medical instrument for a particular medical procedure. If the incorrect medical instrument is provided, as part of the instrument set for the particular medical procedure, delays and/or complications related to the particular medical procedure may occur. If an attribute of the medical instrument is incorrect, which might include providing an inferior grade of instrument for surgical use, the instrument set may be rejected, resulting in further delays. Another problem may occur if the size of the medical instrument is inconsistent with the anatomy of the patient, for example, which may lead to safety concerns. Similarly, retention, inclusion, and/or use of an improperly cleaned or maintained medical instrument may jeopardize the success of any medical procedure.

DETAILED DESCRIPTION OF PREFERRED EMBODIMENTS

Figure 1:
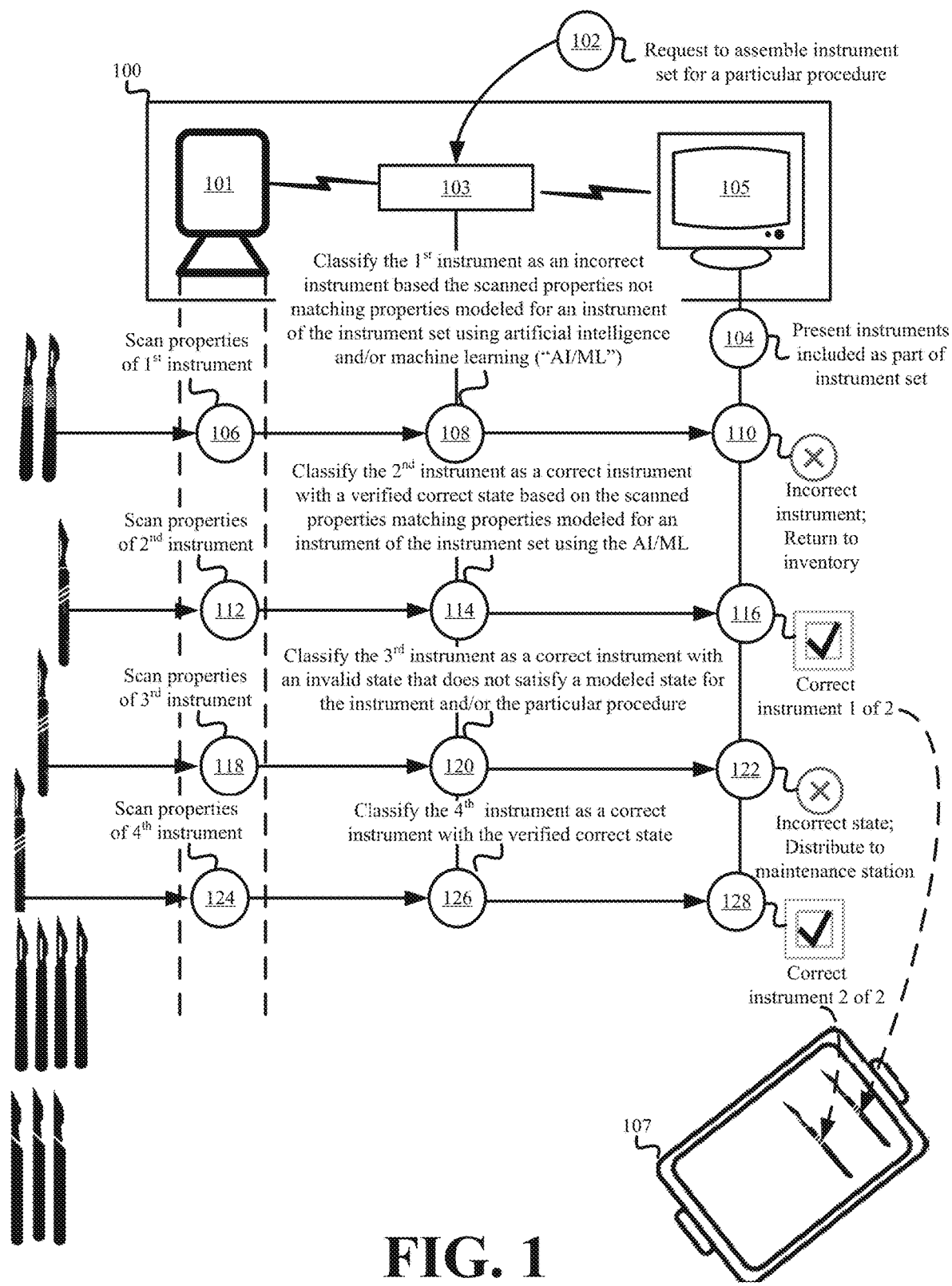
FIG. 1 illustrates an example of automated instrument control in accordance with some embodiments presented herein.

Provided are systems and methods for automated control of medical instruments using artificial intelligence and/or machine learning ("AI/ML"). The systems and methods may use one or more sensors in combination with AI/ML generated models to track and verify the state of medical instruments within a site (e.g., a medical center), and to control the distribution of the medical instruments with correct and verified states for different medical procedures and/or for use by different medical personnel.

In some embodiments, the state verification may include using the data from the sensors and the AI/ML generated models to verify that the correct type, make, and/or model of instrument is selected for a medical procedure, to verify that a selected instrument matches preferences of the medical personnel performing the medical procedure, to verify that a selected instrument is correct for the target patient, and/or to verify that a selected instrument satisfies various state requirements that define whether the instrument is in proper condition for use during the medical procedure. For instance, the systems and methods may include providing an example set of labeled and/or unlabeled training data to one or more supervised or unsupervised AI/ML techniques, and detecting, from the training data using the AI/ML techniques, commonality, patterns, and/or other trends for differentiating between similar instruments of different makes, models, manufacturers, etc., and/or for differentiating between different instrument states. The instrument states may correspond to different defects, contaminants, conditions, properties, calibration, configuration, and/or other variations that may affect a particular instrument. The AI/ML techniques may model probabilities that different characteristic combinations within the example set of training data result in one or more of the differentiated states. The state verification may then include analyzing the sensor data collected from a selected instrument against the AI/ML trained models in order to detect instrument defects and/or issues that may be imperceptible to the human eye and/or that may violate the state requirements.

In some embodiments, controlling the instrument distribution may include adding a selected instrument with correct and verified states for a particular procedure to the instrument set for that particular procedure. Controlling the instrument distribution may further include rerouting a selected instrument with incorrect states (e.g., instrument with detected defects and/or issues) so that the instrument is removed, repaired, cleaned, and/or otherwise temporarily withdrawn from use in medical procedures. The systems and methods may generate notifications and/or messaging to control the instrument distribution, guide technicians in the instrument set assembly, reroute instruments, notify manufacturers of individual defects or widespread issues for necessitating a recall or instrument redesign, and/or executing the actions determined from the AI/ML models and automated analysis.

In some embodiments, the systems and methods may include tracking the routing of instruments within a site and/or the instrument states over time in order to compile additional training data for further refinement of the AI/ML modeling. In other words, the controlled distribution may provide additional training data that may be used to adjust the characteristic combinations within the models used to determine and/or classify the different instrument states.

Additionally, the tracked instrument movements and states may be used to generate predictive models for the lifespans of the different medical instruments. In some embodiments, the predictive models may impact the instrument distribution by predicting the likelihood of instruments experiencing failures, defects, and/or other issues, and by rerouting those instruments from use in medical procedures so that they may repaired, maintained, and/or otherwise remedied before causing harm in a medical procedure, before the issues become unrepairable, and/or before the cost for maintenance increases. The predictive models may identify a repeating issue with a particular instrument, and may be used in triggering a recall or redesign of the particular instrument because of the repeating issue.

Some or all of the processes described herein may be computer-implemented methods, monitored and guided by AI/ML, comprising processor executable instructions stored in the memory of a controller or processor, or otherwise a memory accessible by the controller or processor, whether local or remote. The following description is set forth for explanation to provide an understanding of the various embodiments of the present disclosure. However, as should be apparent, one skilled in the art will recognize that embodiments of the present disclosure may be incorporated into numerous other assemblies, systems, and devices. The embodiments of the present disclosure may include certain aspects each of which may be present in, or performed through the use of, one or more medical instruments, assemblies, or systems thereof. Furthermore, the illustrated example embodiments disclosed or described herein may include more or less structures than depicted and are not intended to be limited to the specific depicted structures. While various portions of the present disclosure are described relative to specific structures, methods, or processes with respect to a medical instrument, assembly, or system using specific labels these labels are not meant to be limiting. Reference will now be made in detail to the present exemplary embodiments, which are illustrated in the accompanying drawing.

FIG. 1 illustrates an example of automated instrument control in accordance with some embodiments presented herein. FIG. 1 illustrates instrument control system 100 comprising one or more sensors 101, controller 103, and user interface ("UI") 105. The same or different instances of UI 105 may be presented on one or more devices.

Instrument control system 100 may be implemented within a medical center, facility, laboratory, and/or another site. Instrument control system 100 may have a localized or distributed implementation. For instance, a localized implementation of instrument control system 100 may include housing each of sensors 101, controller 103, and UI 105 in a single device that is located in a room of the medical site where instrument sets for different medical procedures are assembled. A distributed implementation of instrument control system 100 may include locating the one or more sensors 101 in the one or more rooms or locations where the instrument sets are assembled, repaired, maintained, cleaned, and/or handled, executing controller 103 on a set of remote or "cloud" computing resources, and communicably coupling, via wired or wireless networking, controller 103 to the one or more sensors 101 and/or the one or more instances of UI 105 running on one or more devices of medical personnel within the medical site (e.g., tablet devices, desktop computers, smartwatches, etc.).

Controller 103 may receive (at 102) a request to assemble an instrument set for a particular medical procedure. In this example, the instrument set may be defined to include two units of a particular scalpel from scalpels of different makes and models within the medical site inventory. Other instruments that may be defined as part of the instrument set or that may be included in the instrument inventory may include different types and/or kinds of clamps, scopes, bandages, suturing equipment, monitors, drills, extractors, applicators, forceps, chisels, scoops, hooks, mirrors, mallets, probes, contractors, spreaders, shears, saws, scissors, speculums, suction devices, prosthesis, screws, plates, retractors, and/or other equipment used for different procedures. The different procedures may include different surgeries, operations, examinations, evaluations, treatments, and/or other services provided at the site and/or by the medical personnel.

Controller 103 may modify (at 104) UI 105 to present the instrument set components. Specifically, controller 103 may modify (at 104) UI 105 to present an instruction for a technician to select two of the particular scalpel from the available inventory, and to enter the two units of the particular scalpel as part of assemblage 107 being prepared for the particular medical procedure.

In some embodiments, UI 105 may identify specific locations about assemblage 107 where each unit of the particular scalpel is to be placed. For instance, controller 103, via UI 105, may order the instruments for the instrument set according to their size, expected time of use, and/or dependencies with other instruments. In particular, UI 105 may specify locating orthopedic screws next to a medical plate or a prosthesis that is secured in place by the orthopedic screws.

The technician may select a first scalpel from the available inventory, and the one or more sensors 101 may scan (at 106) the first selected scalpel. In some embodiments, the one or more sensors 101 may include imaging devices that image the first selected scalpel using different wavelengths or frequencies of the electromagnetic spectrum (e.g., visible light, ultraviolet, infrared, x-ray, etc.) that may expose or capture different properties of the first selected scalpel. For instance, visible light images may identify physical features of the first selected scalpel, ultraviolet and/or infrared light images may expose organic and/or chemical contaminants on the first selected scalpel that are not visible to the human eye, and x-ray images may expose structural defects of the first selected scalpel that are not visible to the human eye. In some embodiments, the one or more sensors 101 may include three-dimensional cameras, depth cameras, Light Detection and Ranging ("LiDAR"), and/or super high-resolution cameras for detailed imagery of a fine edge or surface. In some embodiments, the one or more sensors 101 may use lasers, light, sound (e.g., ultrasound), and/or other signaling to measure dimensions, density, rigidity, material composition, refraction, reflectivity, sharpness, and/or other properties of the first selected scalpel and other instruments placed before the one or more sensors 101. In some embodiments, the one or more sensors 101 may include a scale for measuring the weight of a medical instrument.

Accordingly, scanning (at 106) the first selected scalpel may include reading a Radio-Frequency Identification ("RFID") tag, barcode, or other unique identifier of the first selected scalpel, taking one or more images of the first selected scalpel at different wavelengths of the electromagnetic spectrum (e.g., visible, ultraviolet, infrared, x-ray, etc.), and/or measuring different properties (e.g., weight, dimensions, density, material composition, sharpness, etc.) of the first selected scalpel with light, sound, lasers, image analysis, signal analysis, and/or other techniques. The one or more sensors 101 may provide the scanned data to controller 103.

In some embodiments, controller 103 may directly determine if the first selected scalpel is the correct scalpel for the particular medical procedure (e.g., the particular scalpel) based on the scanned data including a unique identifier of the particular scalpel. For instance, the scanned data may include a scan of an RFID, barcode, serial number, Unique Device Identifier ("UDI"), and/or other identifier that directly identifies and/or links to the scalpel make, model, manufacturer, and/or other identifying information. In some embodiments, controller 103 may query a database using the scanned identifier to identify the instrument make, model, manufacturer, and/or other identifying information.

In some embodiments, the first selected scalpel may lack any direct identifying information and/or sensors 101 may be unable to scan (at 106) the unique identifier of the first selected scalpel. In some such embodiments, controller 103 may use the AI/ML generated models to identify the first selected scalpel based on imaged features, measurements, and/or scanned properties of the first selected scalpel. For instance, features, measurements, and/or scanned properties of different instruments may be provided as inputs to one or more neural networks or AI/ML classifiers. The neural networks or AI/ML classifiers may process the input data to determine the specific set of features, measurements, and/or scanned properties that differentiate a particular medical instrument from other medical instruments with a threshold probability (e.g., features, measurements, and/or scanned properties that identify the particular medical instrument with at least an 80% certainty and that identify all other medical instruments with less than a 20% certainty). In some such embodiments, controller 103 may input the scanned data for the first selected scalpel into one or more AI/ML generated models to verify whether the first selected scalpel is the particular scalpel specified for the particular medical procedure. In some embodiments, the AI/ML generated models may also be trained to differentiate between different states of the particular medical instrument. For instance, the training data may include example features, measurements, and/or scanned properties that may be used to differentiate between a sterilized and non-sterilized instance of the particular medical instrument, differentiate between a blunt or sharp instance of the particular medical instrument, differentiate between the particular medical instrument having no defects and having various defects, and/or differentiate between other states of the particular medical instrument with a threshold probability. Accordingly, the one or more AI/ML generated models may also be used to verify the first selected scalpel state (e.g., whether the first selected scalpel state satisfies state requirements or conditions specified for the particular scalpel and/or the particular medical procedure).

Controller 103 may determine (at 108) that the first selected scalpel is of a different make or model than the particular scalpel, and may modify (at 110) UI 105 to reject the inclusion of the first selected scalpel as part of the particular medical procedure instrument set. In some embodiments, UI 105 may provide a message that identifies that the wrong scalpel was selected, and may provide additional identifying information to guide in the selection of the correct scalpel.

The technician may return the first selected scalpel back into inventory in response to the inventory control system 100 direction provided via UI 105. The technician may select a second scalpel from the available inventory, and the one or more sensors 101 may scan (at 112) the second selected scalpel. The one or more sensors 101 may provide the scanned data to controller 103.

Controller 103 may use the AI/ML generated models to verify (at 114) that the second scalpel matches the particular scalpel specified for the particular medical procedure, and to further verify (at 114) that one or more states of the second scalpel satisfy the states of the particular scalpel for the particular medical procedure. For instance, the AI/ML generated models may model a particular sterilization state, sharpness, and/or other conditions for the particular scalpel used as part of the particular medical procedure. Based on a comparison of the scanned data to the AI/ML generated models, controller 103 may determine (at 114) that the second selected scalpel state satisfies the particular scalpel state modeled for the particular medical procedure, and may control the distribution of the second selected scalpel as part of the particular medical procedure by modifying (at 116) UI 105 to accept the inclusion of the second selected scalpel as part of the instrument set for the particular medical procedure. Modifying (at 116) UI 105 may include identifying a location or position for the second selected scalpel on assemblage 107. In response to the confirmation presented in UI 105, the technician may add the second selected scalpel at the identified location or position on assemblage 107 where the instruments for the particular medical procedure are assembled (e.g., a first destination). In some embodiments, the one or more sensors 101 may verify the correct placement of the second selected scalpel to the identified location or position on assemblage 107.

Controller 103, via UI 105, may provide additional messaging that directs the technician to select and add another unit of the second scalpel at a different location or position on assemblage 107. The technician may select a third scalpel from the available inventory, and the one or more sensors 101 may scan (at 118) the third selected scalpel. The one or more sensors 101 may provide the scanned data to controller 103.

Controller 103 may use the AI/ML generated models to verify (at 120) that the third scalpel matches the particular scalpel specified for the particular medical procedure and/or is of the same make and model as the particular scalpel and the second selected scalpel. However, controller 103 may determine (at 120) that one or more states of the third selected scalpel do not satisfy the modeled states for the particular scalpel. For example, the scanned data of the third selected scalpel may reveal traces of biological matter that indicate an improperly sterilized instrument. Accordingly, the sterilization state of the third selected scalpel may not satisfy a modeled sterilization state for the particular scalpel and/or the particular medical procedure (e.g., for using the particular scalpel as part of the particular medical procedure). As another example, the scanned data of the third selected scalpel may measure the alignment of the scalpel cutting edge, and the measurements may not satisfy a sharpness state modeled for the particular scalpel or the particular medical procedure.

Accordingly, controller 103 may modify (at 122) UI 105 to reject the inclusion of the third selected scalpel as part of the particular medical procedure instrument set based on the invalid instrument state, and/or may control the distribution of the third selected scalpel by routing the third selected scalpel to a cleaning station for sterilization (e.g., a second destination), maintenance (e.g., a third destination) for sharpening, and/or another location or station (e.g., a fourth destination) within the site to remedy the invalid state. Additionally, controller 103 may update an inventory tracking system to assign the third selected scalpel from the available inventory to a new location or station within the site.

The technician may select a fourth scalpel from the available inventory, and the one or more sensors 101 may scan (at 124) the fourth selected scalpel. The one or more sensors 101 may provide the scanned data to controller 103.

Controller 103 may use the AI/ML generated models to verify (at 126) that the fourth scalpel matches the particular scalpel specified for the particular medical procedure, and to further verify (at 126) that one or more states of the fourth scalpel satisfy the states of the particular scalpel and/or the particular medical procedure. Controller 103 may determine (at 126) that the fourth selected scalpel state satisfies the particular scalpel state for the particular medical procedure, and may modify (at 128) UI 104 to accept the inclusion of the fourth selected scalpel as part of the instrument set for the particular medical procedure. Moreover, controller 103 may track that two units of the particular scalpel have been selected and/or loaded to assemblage 107 for the particular medical procedure, and may update the inventory tracking system to assign the second selected scalpel and the fourth selected scalpel from the available inventory to the particular medical procedure.

In this manner, instrument control system 100 may control the distribution of the correct instruments with the correct states for use as part of the particular medical procedure. Specifically, instrument control system 100 may automatically differentiate between and/or control the distribution of instruments that may appear similar to the technician or a human, but that could create unexpected or undesired results if used for the particular medical procedure. Similarly, instrument control system 100 may automatically differentiate between and/or control the distribution of the same instrument with different states that may be imperceptible to the technician or a human, but that also could create unexpected or undesired results if used for the particular medical procedure. For instance, defects or biological contaminants on a medical instrument could result in failures, harm, damage, infection, and/or other unintended consequences.

Figure 2:
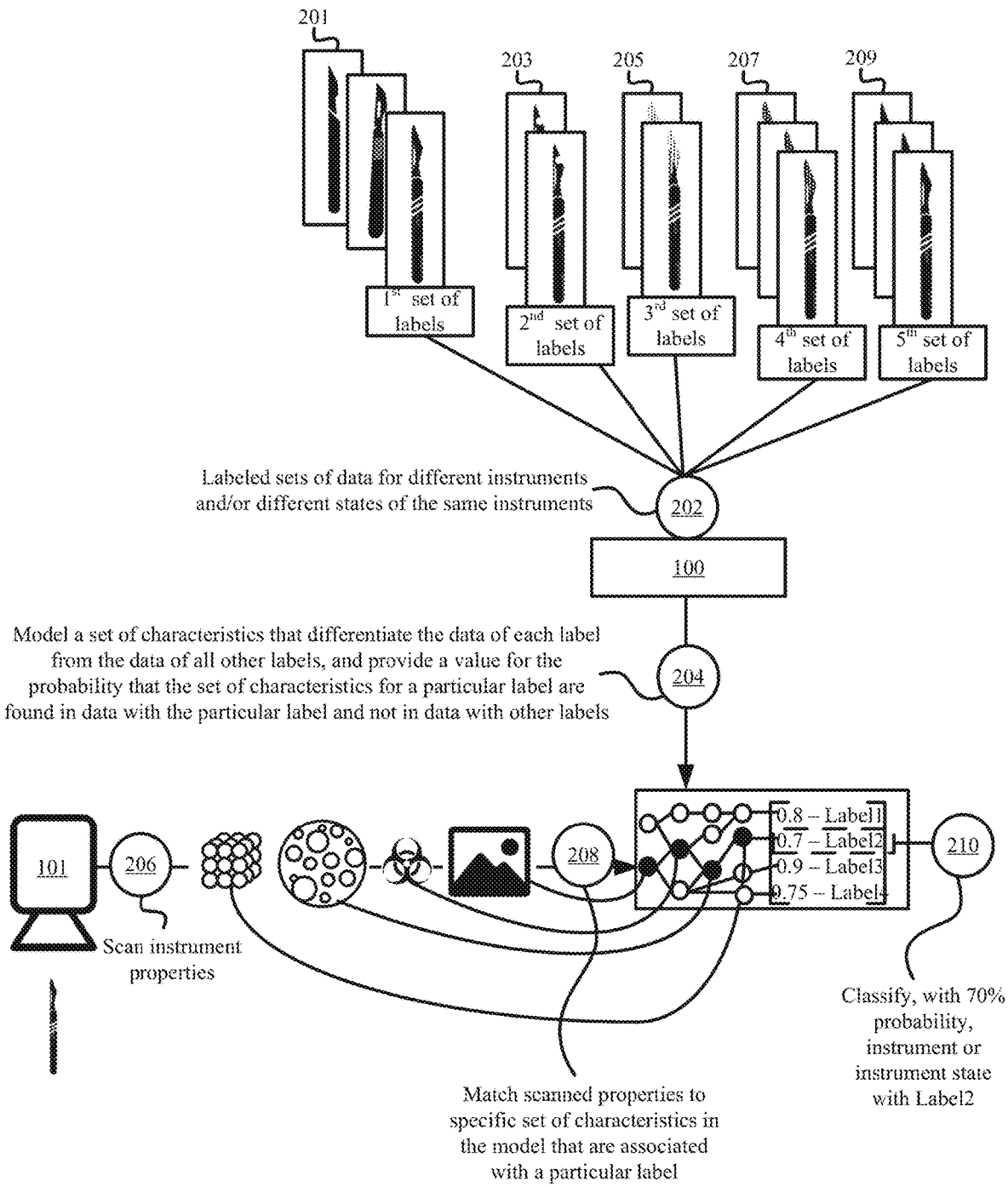
FIG. 2 illustrates an example for differentiating between different instruments and/or different instrument states based on supervised machine learning performed over a labeled set of training data in accordance with some embodiments presented herein.

In some embodiments, instrument control system 100 may perform supervised machine learning over a labeled set of training data to generate the probabilistic and/or predictive models that are used for differentiating between different instruments and/or different instrument states. FIG. 2 illustrates an example for differentiating between different instruments and/or different instrument states based on supervised machine learning performed over a labeled set of training data in accordance with some embodiments presented herein.

As shown in FIG. 2, different labeled sets of data 201, 203, 205, 207, and 209 may be provided (at 202) to a neural network and/or AI/ML classifier of instrument control system 100. Different neural networks and/or AI/ML classifiers may be used depending on the modeling that is desired and/or the data that is provided (at 202). For instance, inventory control system 100 may use one or more Convolutional Neural Networks ("CNNs"), Recurrent Neural Networks ("RNNs"), Multilayer Perceptrons ("MLPs"), Long Short Term Memory ("LSTM"), and/or other AI/ML techniques to detect different commonality, patterns, and/or trends in the labeled sets of data 201, 203, 205, 207, and 209 that differentiate between different instruments and/or various states of different instruments. The data may be in the form of images, sound profiles, measurements (e.g., dimensions, weight, density, material composition, etc.), and/or text (e.g., make, model, and/or descriptive characteristics). The data may include values for properties that are imaged, measured, and/or otherwise scanned by sensors 101 of inventory control system 100.

Instrument control system 100 may retrieve one or more of the labeled sets of data 201, 203, 205, 207, and 209 from the Internet and/or different network-accessible sources including websites or databases of medical instrument manufacturers. For instance, instrument control system 100 may scrape images, text (e.g., descriptive and/or identifying information, measurements, dimensions, properties, etc.), and/or other data for new medical instruments from a manufacturer's website or database to facilitate the automated detection and/or identification of those new medical instruments. Instrument control system 100 may also retrieve one or more of the labeled sets of data 201, 203, 205, 207, and 209 from a system administrator that compiles the data from the one or more sensors 101 and/or other sources, and that provides labels to differentiate the data.

In some embodiments, the labels may identify a particular instrument make, model, manufacturer and/or other identifying information that may be used to differentiate that particular instrument from other instruments (e.g., differentiate a first clamp of a first manufacturer from a second clamp of a second manufacturer, differentiate the first clamp of the first manufacturer from a third clamp of the first manufacturer, etc.). In some embodiments, the labels may include the unique identifier that is associated with each unique medical instrument (e.g., the UDI or serial number). In some embodiments, the labels may identify different states of a particular medical instrument. For instance, an image within the labeled set of data may include a first label for the UDI that uniquely identifies the make, model, and/or manufacturer of the imaged instrument, a second label that identifies a first state of the imaged instrument (e.g., instrument is imaged in a fully sterilized state), and a third label that identifies a different second state of the imaged instrument (e.g., instrument contains a particular defect that is shown in the image).

First labeled set of data 201 may include identifying data (e.g., images, measurements, and/or properties) and labels for differentiating between different scalpels (e.g., scalpels from different manufacturers, of different makes and models, of different dimensions, with different features, etc.). Second, third, fourth, and fifth labeled sets of data 203, 205, 207, and 209 may include identifying data and labels for differentiating between different states of a particular scalpel. For instance, second labeled set of data 203 may include example data and labels for the particular scalpel in a new state and various used states (e.g., new, after use in 5 procedures, after use in 10 procedures, etc.), third labeled set of data 205 may include example data for the particular scalpel in various unsterilized or unsanitary states (e.g., examples of the particular scalpel with various biological or chemical contaminants), fourth labeled set of data 207 may include example data for the particular scalpel with various defects (e.g., chipped blade, bent blade, incorrect blade, etc.), and fifth labeled set of data 209 may include example data for the particular scalpel with different configurations (e.g., blade for small incisions versus blade for large incisions, blade for first procedure versus blade for second procedure, etc.).

The neural network and/or AI/ML classifier may compare the data from each set 201, 203, 205, 207, and 209 with a particular label to the data with other labels from the same set 201, 203, 205, 207, and 209 to detect commonality, patterns, trends, and/or other characteristics that differentiate the data of the particular label from the data of all other labels. The neural network and/or AI/ML classifier may generate (at 204) a model based on the detected commonality, patterns, trends, and/or other characteristics. Specifically, the neural network and/or AI/ML classifier may generate (at 204) a model with different sets of characteristics that differentiate the data of each label from the data of all other labels, and with a value for the probability that the set of characteristics detected for a particular label are found in data with the particular label and not in data with other labels. The probability values may be calculated based on a number of times each particular set of characteristics from the different sets of characteristics is found in the set of data related to one or more instrument states classified using that particular set of characteristics and the set of data related to other instrument states not classified using that particular set of characteristics.

For example, the neural network and/or AI/ML classifier may determine that most scalpels have blades with similar shapes. However, the handles of different scalpels may differ in visual appearance and weight. Accordingly, the neural network and/or AI/ML classifier may generate a classification model with different weight and visual feature combinations that identify different scalpels (e.g., a first set of labels) with different probabilities based on the degree with which the weight and visual feature combinations differentiate one scalpel from other scalpels.

As another example, the neural network and/or AI/ML classifier may determine that an unsterilized or unsanitary scalpel is less reflective than a sterilized or sanitary scalpel, has certain visual markers in ultraviolet imagery that do not appear in ultraviolet imagery of a sterilized or sanitary scalpel, and/or has various color components (e.g., rusting, staining, and/or other discoloration) in visible light imagery that do not appear in visible light imagery of a sterilized or sanitary scalpel. The neural network and/or AI/ML classifier may generate a sterilization model that differentiates between different sterilization states (e.g., a second set of labels) of a particular scalpel based on the commonality and/or patterns detected in the reflectivity, ultraviolet light image characteristics, and/or visible light image characteristics for the different sterilization states in the labeled set of data.

Once the models have been generated, instrument control system 100 may use the one or more sensors 101 to scan (at 206) an instrument. The scanned data (e.g., detected properties of the instrument) may be input to the generated models, and may be matched (at 208) against the different characteristic combinations that are modeled for differentiating between different instruments and/or instrument states. As shown in FIG. 2, a subset of the scanned data may match (at 208) to a particular combination of characteristics within a generated model. The particular combination of characteristics may be associated with one or more labels that classify (at 210) the instrument and/or the instrument state.

Figure 3:
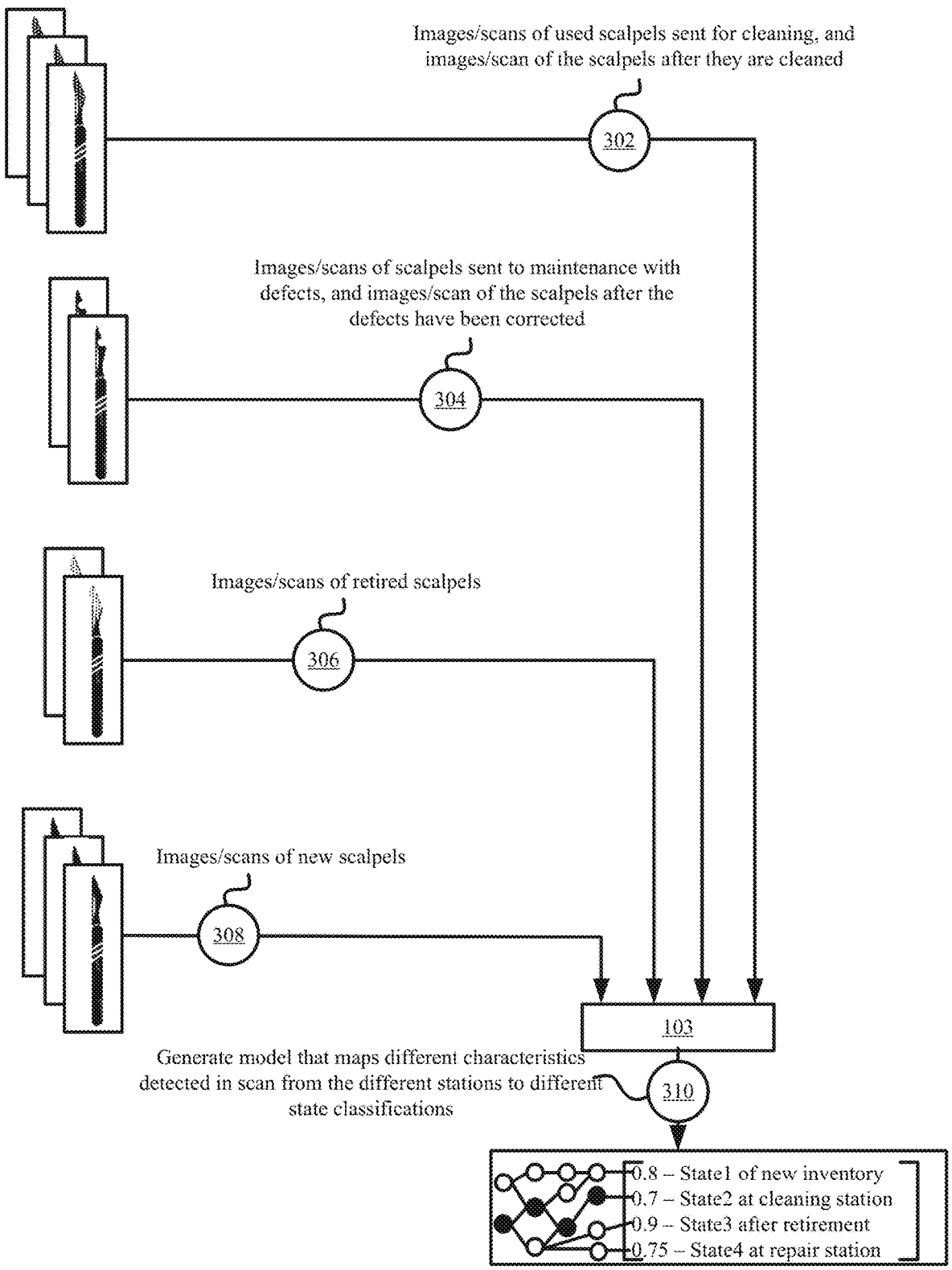
FIG. 3 illustrates an example for differentiating between different instruments and/or different instrument states based on unsupervised machine learning performed over an unlabeled set of training data in accordance with some embodiments presented herein.

In some embodiments, instrument control system 100 may perform unsupervised machine learning over an unlabeled set of training data to generate the probabilistic and/or predictive models that may be used to differentiate between different instruments and/or instrument states. FIG. 3 illustrates an example for differentiating between different instruments and/or different instrument states based on unsupervised machine learning performed over an unlabeled set of training data in accordance with some embodiments presented herein.

Instrument control system 100 may perform the unsupervised machine learning based on different states that instrument control system 100 tracks for different medical instruments. For instance, the one or more sensors 101 may be located at a cleaning station, a refurbishment or repair station, inventory retirement station, and/or other stations that the instruments may move to during their lifecycles, and controller 103 may receive scanned data from each set of sensors 101 at each station and may tag the received scanned data with a station and/or location tag. As shown in FIG. 3, controller 103 may receive (at 302) images and/or scans of different instruments before and/or after they have been cleaned at the cleaning station, may receive (at 304) images and/or scans of different instruments with defects before and/or after the instruments are repaired at the refurbishment or repair station, may receive (at 306) images and/or scans of different instruments after they are removed from available inventory at the inventory retirement station, and may receive (at 308) images and/or scans of instruments in a new state.

The images and/or scans from the different stations may provide controller 103 and/or the AI/ML techniques with comparative data from which characteristic combinations of differentiated instruments and/or instrument states may be determined. Accordingly, controller 103 may provide the images and/or scans from the different stations to the neural network and/or AI/ML classifier. The neural network and/or AI/ML classifier may compare the images and/or scans from the different stations to detect different sets of scanned properties and/or characteristics with which to differentiate the same instrument with different states and the same station or different stations. For instance, the neural network and/or AI/ML classifier may compare one or more scans of one or more instruments after use in a medical procedure and before cleaning to one or more scans of the same one or more instruments after cleaning at the cleaning station or may compare scans of the same instrument when it is entered or removed from storage and/or before or after use in medical procedure.

The neural network and/or AI/ML classifier may detect a first set of characteristics present in the scanned data of an instrument before it is cleaned (e.g., features, measurements, and/or scanned properties that are repeatedly found in the instrument scans after use in medical procedure), and a different second set of characteristics present in the scanned data of the same instrument after it is cleaned at the cleaning station and entered back into available inventory (e.g., features, measurements, and/or scanned properties that are not found in the scans after use in medical procedure and that are present in the scans of the same instrument after it is cleaned). The neural network and/or AI/ML classifier may generate (at 310) a model that differentiates between an unclean state and a clean state based on the differences between the first set of characteristics and the second set of characteristics. Accordingly, instrument control system 100 may leverage its ability to track where instruments are within a site, and to use the tracking information as pseudo-labels for differentiating between instrument states.

In some embodiments, instrument control system 100 may generate a different classification model for each instrument and/or each instrument state. For instance, instrument control system 100 may use the AI/ML techniques to train a first model for differentiating between clamps of the same manufacturer and/or other manufacturers, a second model for differentiating between scopes of the same manufacturer and/or other manufacturers, a third model for differentiating between a sterilized and unsterilized state of a particular clamp or a set of clamps, a fourth model for differentiating between a particular clamp or a set of clamps with defects and without defects, and/or additional models for differentiating between different states of the clamps, scopes, and/or other instruments.

Figure 4:
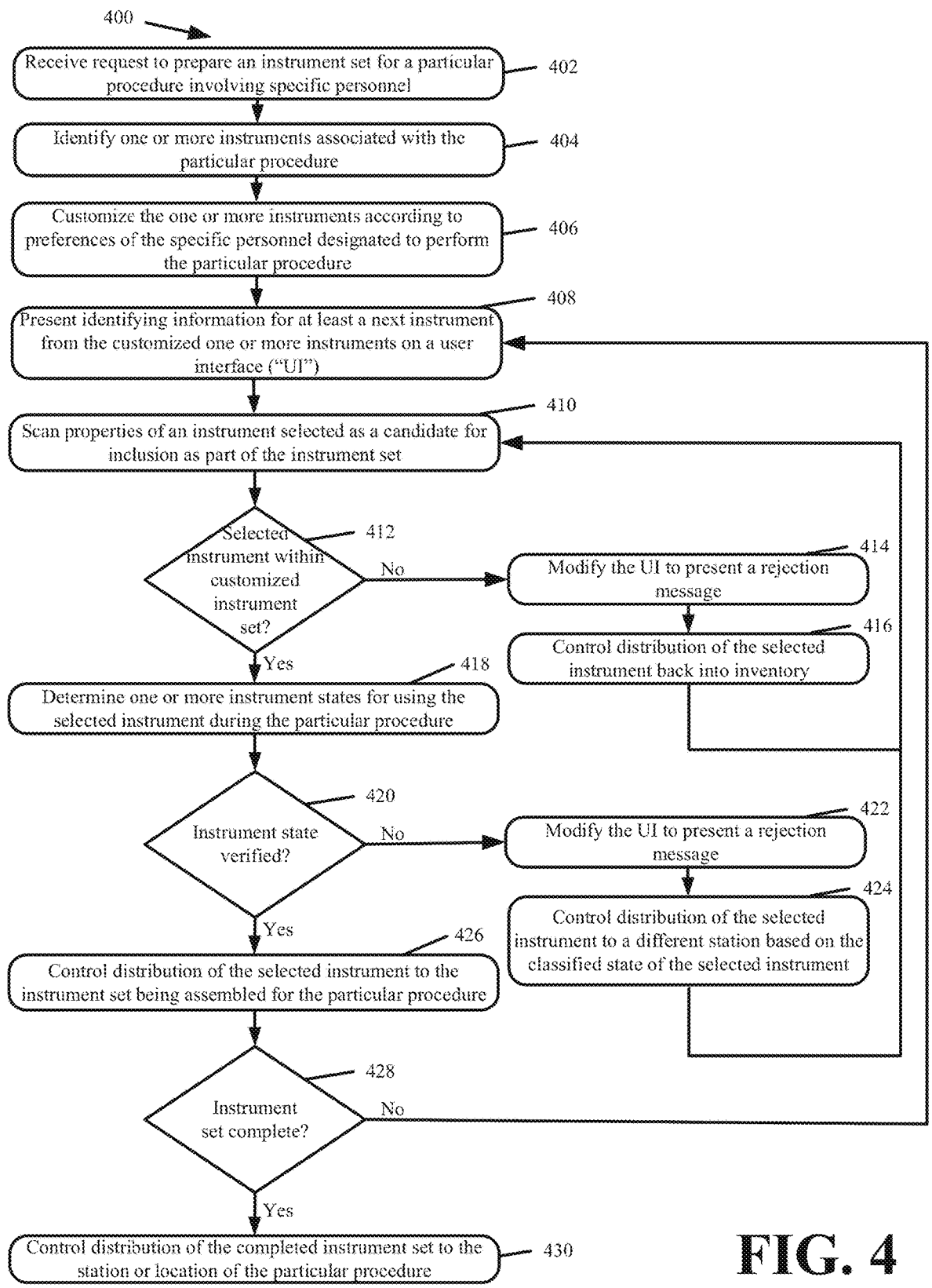
FIG. 4 presents a process for controlling the distribution of instruments based on artificial intelligence and/or machine learning ("AI/ML") generated models in accordance with some embodiments presented herein.

FIG. 4 presents a process 400 for controlling the distribution of instruments based on AI/ML generated models in accordance with some embodiments presented herein. Process 400 may be implemented by instrument control system 100. In particular, process 400 may be implemented via the one or more sensors 101, controller 103, and UI 105 of instrument control system 100.

Process 400 may include receiving (at 402) a request to prepare an instrument set for a particular procedure involving specific personnel. The request may identify one of different types of surgeries, operations, examinations, evaluations, treatments, etc., may include the names or identifiers for one or more personnel scheduled to perform the particular procedure, and/or may include non-confidential information about the target patient (e.g., age, sex, height, weight, etc.). For instance, a technician may input one or more identifiers for the particular procedure, personnel performing the particular procedure, and the target patient via UI 105, and controller 103 may determine the proper instrument set based on the one or more identifiers.

Process 400 may include identifying (at 404) one or more instruments for the particular procedure. The one or more instruments may include tools, devices, and/or different apparatus that are used or that may be used during the particular procedure. For instance, backup instruments may be specified in the event a primary instrument breaks or secondary personnel is needed to assist primary personnel. The instruments may include different types and/or kinds of clamps, scopes, scalpels, bandages, suturing equipment, monitors, drills, extractors, applicators, forceps, chisels, scoops, hooks, mirrors, mallets, probes, contractors, spreaders, shears, saws, scissors, speculums, suction devices, screws, prosthesis, retractors, medical plates, and/or other equipment used in the performance of the particular procedure.

In some embodiments, the identification (at 404) may include obtaining the names or unique identifiers (e.g., UDI) of the instruments and a quantity for each identified instrument. In some embodiments, the identification (at 404) may include identification of specific set of instrument properties (e.g., type, make, model, size, weight, identifying features, etc.).

In some embodiments, instrument control system 100 may be programmed with different lists of instruments for different procedures. For instance, a specific first scalpel of a first manufacturer may be specified for a first surgery, and a specific second scalpel a second manufacturer may be specified for a second surgery. In some such embodiments, the identification (at 404) may involve querying a database with an identifier of the particular procedure (e.g., the procedure name, medical coding value, etc.), and receiving a list of instruments that are defined as part of the instrument set for that particular procedure in the database. In some embodiments, the particular procedure may be associated with a specific set of instruments provided by a specific manufacturer. For instance, a first instrument of the specific manufacturer may require or may only be compatible with a second instrument of the specific manufacturer. Accordingly, to maximize safety and effectiveness of the particular procedure, the instrument set may include only instruments of the specific manufacturer.

Process 400 may include customizing (at 406) the one or more instruments according to preferences of the specific personnel that are designated to perform the particular procedure and/or attributes of the target patient. In some embodiments, instrument control system 100 may track instrument preferences of different personnel for different procedures. For instance, a first surgeon performing a particular surgery may prefer using a first clamp, whereas a second surgeon performing the same particular surgery may prefer using a different second clamp. Similarly, instruments of the instrument set may be customized (at 406) depending on whether the target patient is a child or adult, has specific allergies or sensitives, and/or has various other conditions that may be related or unrelated to the particular procedure. Accordingly, customizing (at 406) the one or more instruments may include swapping out an identification of one or more instruments that are specified for the particular procedure with substitute instruments that the specific personnel prefers for the particular procedure and/or that maximize safety and effectiveness for the target patient. If no preferences are tracked for the specific personnel, then instrument control system 100 may retain the default one or more instruments that were specified for the particular procedure.

Process 400 may include presenting (at 408) identifying information for at least a first instrument from the customized one or more instruments on UI 105. UI 105 may present (at 408) an image of the first instrument, text for the name, make, model, manufacturer, and/or other identifying information, visual markers to identify placement or position of the first instrument in inventory, and/or other visual or audio queues for assisting a technician in selecting the first instrument and/or assembling the instrument set for the particular procedure. UI 105 may be presented on a display at an instrument set assembly station, a device worn by a worker, a tablet or other portable device in the proximity of the worker, devices used by the specific personnel, and/or on displays of administrators that oversee the execution of the particular procedure and/or other procedures.

Process 400 may include scanning (at 410) properties of a selected instrument prior to the selected instrument being included as part of the instrument set. In some embodiments, the UI 105 may direct a worker in selecting an instrument from inventory that matches the first instrument presented (at 408) in the UI 105. The worker may select the instrument, move the instrument under the one or more sensors 101, and the one or more sensors 101 may scan (at 410) the properties of the selected instrument.

In some embodiments, the one or more sensors 101 may track movements of the worker, may detect when the worker selects and/or removes an instrument from inventory, may scan (at 410) the selected instrument without the worker having to directly position the selected instrument underneath or before the one or more sensors 101, and may further detect where the worker places the selected instrument (e.g., places the selected instrument onto a tray or container designated for the instrument set, returns the selected instrument back into inventory, router the selected instrument to a different station, etc.). In some other embodiments, the one or more sensors 101 may automatically detect when an instrument is selected and/or brought before the sensors 101, and the sensors 101 may perform one or more scans upon detecting the selected instrument. The scanned data and/or instrument properties may be transmitted from the one or more sensors 101 to controller 103 for processing.

Scanning (at 410) the properties may include using the one or more sensors 101 in conjunction with structured light, different wavelengths of the electromagnetic spectrum (e.g., visible light, infrared, ultraviolet, x-ray, etc.), lasers, radio waves, sounds, and/or other signaling to image the selected instrument from different angles, sides, or positions (e.g., top, side, bottom, front, etc.), obtain various measurements of the selected instrument (e.g., height, length, width, weight, density, reflectivity, material composition, etc.), obtain identifying information (e.g., read an RFID, barcode, serial number, Quick Response ("QR") code, or other identifier), and/or detect other characteristics of the selected instrument. For instance, a visible light image may identify visible features that aid in identifying the selected instrument, an ultraviolet light image may expose biological or organic matter on the selected instrument that cannot be seen with visible light, an x-ray image may identify the structural composition and/or material defects of the selected instrument, and LiDAR or a super high-resolution image may identify properties relevant to the working condition of the selected instrument.

Process 400 may include verifying (at 412) whether the selected instrument is the first instrument from the customized one or more instruments specified for the particular procedure. The verification (at 412) may be based on the properties that are scanned (at 410) by the one or more sensors 101.

In some embodiments, controller 103 may directly identify the selected instrument from the scanned properties. For instance, the scanning (at 410) may read an RFID tag, serial number, UDI, and/or another unique identifier of the selected instrument. Controller 103 may query an inventory database using the unique identifier to obtain the make, model, manufacturer, and/or other identifying information of the selected instrument, and may compare the obtained identifying information against the identifying information of the first instrument for the particular procedure. In response to the identifying information and/or unique identifier obtained from the scanning (at 410) of the selected instrument matching (e.g., same make, model, and manufacturer) the identifying information and/or unique identifier for an instrument specified as part of the customized instrument set for the particular procedure, then controller 103 may verify (at 412) that the worker selected a correct instrument for the particular procedure.

In some embodiments, the scanned properties of the selected instrument may not directly identify the selected instrument. For instance, the unique identifier may be blocked from the one or more sensors 101 or the selected instrument may lack an RFID tag, engraving, or other marking with the unique identifier.

In some such embodiments, controller 103 may input the scanned properties into one or more of the probabilistic models created for differentiating between different instruments. The scanned properties may match different combinations of modeled identification characteristics within the probabilistic models.

Each model may output a vector. The vector may include a probability value for the degree or amount with which the scanned properties of the selected instrument match the characteristic combinations that the AI/ML modeling uses to differentiate one instrument from other instruments.

Controller 103 may inspect the vector probability values to determine if the AI/ML modeling classifies the scanned properties to match the properties of the first instrument from the customized one or more instruments with at least a threshold probability. If the scanned properties of the selected instrument match with the threshold probability to the identifying characteristics of the first instrument, then controller 103 may verify (at 412) that the worker selected a correct instrument for the particular procedure.

In response to unsuccessfully verifying (at 412—No) the selected instrument as the first instrument or any instrument of the customized one or more instruments for the particular procedure, process 400 may include modifying (at 414) UI 105 to present a rejection message and to prevent the inclusion of the selected instrument as part of the instrument set for the particular procedure. In other words, UI 105 may indicate that the wrong instrument was selected, and may present additional identifying information for selecting the correct instrument. Process 400 may include controlling (at 416) distribution of the selected instrument back into inventory and/or storage (e.g., a first destination). For instance, controller 103 may modify UI 105 to notify the worker to return the selected instrument back into the available inventory and to select a different instrument.

In response to successfully verifying (at 412—Yes) the selected instrument as the first instrument or an instrument from the customized one or more instruments for the particular procedure, process 400 may include determining (at 418) one or more instrument states for using the selected instrument as part of the particular procedure. In some embodiments, the instrument states may be defined for each instrument and/or for each procedure. For instance, a procedure may be defined with a protocol that specifies a set of required states that each instrument used as part of the procedure must satisfy.

Controller 103 may query a database or a procedure definition to obtain the one or more instrument states for the selected instrument and/or use of the selected instrument as part of the particular procedure. The one or more instrument states may specify different sterilization states, operational characteristics, material properties, usage history, defect allowability, a specific configuration, a specific calibration, and/or other constraints or requirements for the selected instrument and/or its use as part of the particular procedure. For instance, the sterilization state for using a particular instrument in a first procedure may require that the particular instrument have been sterilized with one or more chemicals before being wrapped in a protective cover, whereas the sterilization state for using the same particular instrument in a second procedure may require that the particular instrument have been wiped with alcohol or a particular disinfectant.

Process 400 may include verifying (at 420) whether the selected instrument satisfies the instrument states specified for that instrument and/or the particular procedure. To perform the instrument state verification (at 420), controller 103 may input the scanned properties of the selected instrument into one or more of the probabilistic models created for differentiating between different states of the selected instrument.

The scanned properties may match different combinations of modeled state characteristics within the probabilistic models. Each model may output a vector with one or more probability values for the degree or amount with which the scanned properties of the selected instrument match the characteristic combinations that the AI/ML modeling uses to differentiate between different states of the selected instrument. In response to the scanned properties of the selected instrument matching with a threshold probability to each of the instrument states specified for that instrument and/or the particular procedure, controller 103 may verify (at 420) that the selected instrument states satisfy the protocols and/or requirements for using the selected instrument as part of the particular procedure.

In some embodiments, verifying (at 420) the instrument state may include verifying that the selected instrument is configured with a specific set of attributes, is calibrated according to a desired specification, and/or is assembled in a specified manner. For example, the instrument may be an electrocautery pen, and verifying (at 420) the instrument state may include verifying whether the electrocautery pen has been set to a specific operating temperature. As another example, the instrument may be a defibrillator, and verifying (at 420) the instrument state may include verifying whether the defibrillator has been set to a specific voltage or output. As yet another example, the instrument may be a drill, and verifying (at 420) the instrument state may include verifying whether a specific drill bit has been attached to the drill.

In response to unsuccessfully verifying (at 420—No) the instrument state of the selected instrument, process 400 may include modifying (at 422) UI 105 to present a rejection message and to prevent the inclusion of the selected instrument as part of the instrument set for the particular procedure. In other words, the modeling of the instrument state based on the scanned properties may indicate that the selected instrument, although being the correct instrument for the particular procedure, is defective, unsafe, and/or not in a desired working condition for the particular procedure.

Process 400 may include controlling (at 424) distribution of the selected instrument to a different station based on the classified state of the selected instrument (e.g., a second destination). For instance, if the modeling indicates, with a threshold probability, that the selected instrument is not properly sterilized (e.g., contains biological or organic contaminants), then controller 103 may modify UI 105 to direct the worker in entering the selected instrument into a container, bin, or other receptacle for instruments pending sterilization. Similarly, if the modeling indicates, with a threshold probability, that the selected instrument contains one or more defects, then controller 103 may modify UI 105 to direct the technician in transferring the selected instrument to a repair station. Additionally, controller 103 may update the tracking of the selected instrument to identify that the instrument has been removed from the available inventory and has been allocated to the different station and/or workflow for sterilization, repair, removal from service, and/or operations.

In some embodiments, modifying (at 422) UI 105 and/or controlling (at 424) the distribution of the selected instrument may include tracking a set of instruments in need of certain repairs, maintenance, cleaning, and/or other operations. In some such embodiments, controller 103 may notify the proper personnel to initiate the needed operations via UI 105. For instance, controller 103 may provide a wireless message to a device of a third-party service provider that identifies the instruments needing repairs, the location of the instruments, and the list of repairs for each instrument. In response to the messaging, the third-party service provider may retrieve the instruments from the specified location, and may perform the repairs before returning the instruments back into inventory.

Controller 103 may also track issues with different instruments, and may notify a manufacturer of the tracked issues. Alternatively, if controller 103 tracks certain repeating issues with different units of the same instrument, controller 103 may trigger a recall of that instrument from use. Controller 103 may issue the recall messaging internally so that any units of the instrument detected by the one or more sensors 101 are automatically routed out from inventory and into maintenance. Controller 103 may issue the recall messaging externally by contacting the manufacturer of the instrument with the repeating issues. The recall messaging may identify the tracked issues and/or ratio of issues with that instrument or may the component that is a source cause of the repeating issues so that the instrument may be redesigned.

In response to successfully verifying (at 420—Yes) that the selected instrument state satisfies the requirements for the first instrument and/or the particular procedure, process 400 may include controlling (at 426) distribution of the selected instrument to the instrument set being assembled for the particular procedure (e.g., a third destination). Controlling (at 426) the distribution of the selected instrument to the instrument set may include modifying UI 105 to provide a confirmation message that the selected instrument should be included with the instrument set. Additionally, UI 105 may identify a precise location or position at which to include the selected instrument as part of the instrument set. Accordingly, the instrument set may be ordered or arranged according to a desired layout for the particular procedure and/or preferences of the personnel performing the particular procedure. The ordering or arrangement may make access to related or dependent instruments easier, may identify differences between the instruments (e.g., larger instruments above smaller instruments), and/or may specify an order of use for the particular procedure (e.g., place a first used instrument before an instrument that will be used after the first used instrument). Controller 103 may update the tracking of the selected instrument to identify that the instrument has been removed from the available inventory and has been allocated to the particular procedure.

Process 400 may include determining (at 428) if the instrument set, after inclusion of the selected instrument, includes all of the instruments of the one or more customized instruments for the particular procedure and/or the specific personnel performing the particular procedure. In response to determining (at 428—No) that the instrument set is incomplete, process 400 may include presenting (at 408) identifying information for a next instrument from the customized one or more instruments on UI 105, and performing the various verifications to ensure that the correct instrument with the correct state is added to the instrument set. In response to determining (at 428—Yes) that the instrument set is complete, process 400 may include controlling (at 430) the distribution of the completed instrument set to the station or location where the particular procedure is to take place (e.g., a fourth destination). For instance, controller 103 may modify UI 105 to instruct the worker to deliver the instrument set to a particular operating room.

Figure 5:
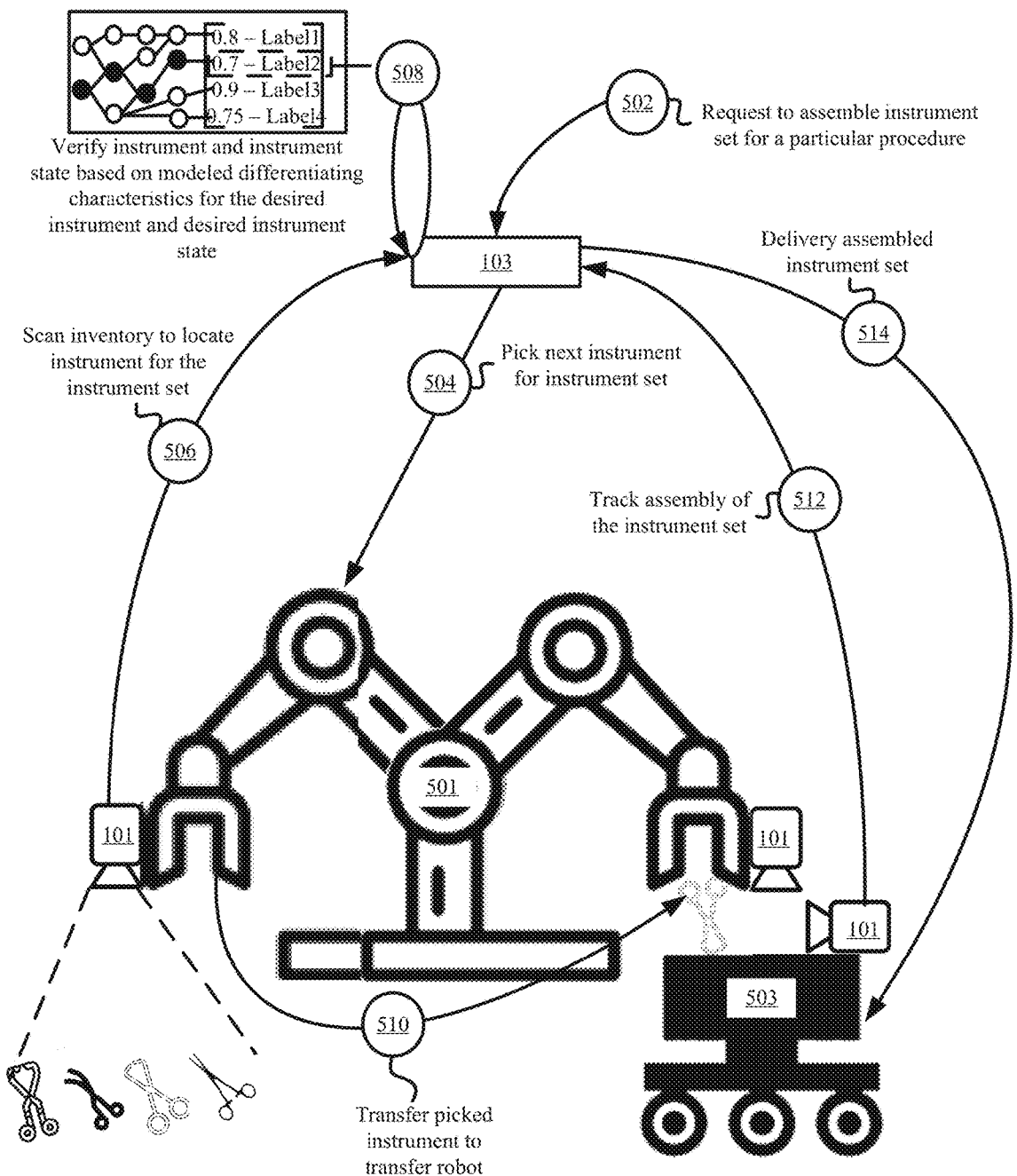
FIG. 5 illustrates an example of a fully autonomous inventory control system in accordance with some embodiments presented herein.

In some embodiments, inventory control system 100 may control the distribution of instruments within a site by controlling one or more robots that assemble the instruments and/or that transfer the instruments between different stations and/or locations in the site. FIG. 5 illustrates an example of a fully autonomous inventory control system 100 in accordance with some embodiments presented herein.

As shown in FIG. 5, inventory control system 100 may include one or more picking robots 501 and one or more transfer robots 503. Picking robots 501 and/or transfer robots 503 may be integrated with one or more sensors 101 and/or controller 103.

Controller 103 may receive (at 502) a request to assemble an instrument set for a particular procedure. Controller 103 may direct (at 504) picking robot 501 in selecting a next instrument of the instrument set from available inventory.

In response, picking robot 501 may move the articulating arm with sensors 101 over the available inventory. Sensors 101 of picking robot 501 may continually scan (at 506) the instruments in the available inventory until the next instrument is located. Specifically, sensors 101 may send the scanned data to controller 103.

Controller 103 may perform a lookup of the scanned data and/or may compare (at 508) the scanned data against the different models to identify the instruments and instrument sets. In some other embodiments, picking robot 501 may map the location of each instrument in storage, may move directly to the location of the next instrument in storage, may select the next instrument, and may scan (at 506) the selected instrument to verify that the selected instrument state satisfies the state specified for the next instrument and/or the particular procedure.

Once the correct instrument with the required state is located, controller 103 may control (at 510) picking robot 501 in picking and transferring the picked instrument to transfer robot 503. In some embodiments, transfer robot 503 may include a tray, container, and/or other receptacle on which the instrument set for the particular procedure is assembled.

Controller 103 may track (at 512) the instruments that have been transferred to transfer robot 503 based on scanned data collected from sensors 101 of picking robot 501 after depositing an instrument in the receptacle of transfer robot 503 and/or sensors 101 of transfer robot 503 detecting entry of a new instrument in the receptacle. In response to determining that the instruments of the instrument sets with the correct states have been assembled in the receptacle of transfer robot 503, controller 103 may control (at 514) transfer robot 503 in delivering the instrument set to the location at which the particular procedure is performed.

In some embodiments, inventory control system 100 may operate from two or more stations or locations within a site where the instruments are handled. In particular, sensors 101 of instrument control system 100 may be deployed at the different stations or locations, and may be used to scan the instruments at the different stations or locations. The distributed presence of inventory control system 100 may allow for precise tracking of the instruments within the site, precise tracking of the instrument states including remaining useful life, and/or a continual feedback loop of training data for improving the AI/ML generated models to better differentiate between the different instruments and/or the different instrument states.

Figure 6:
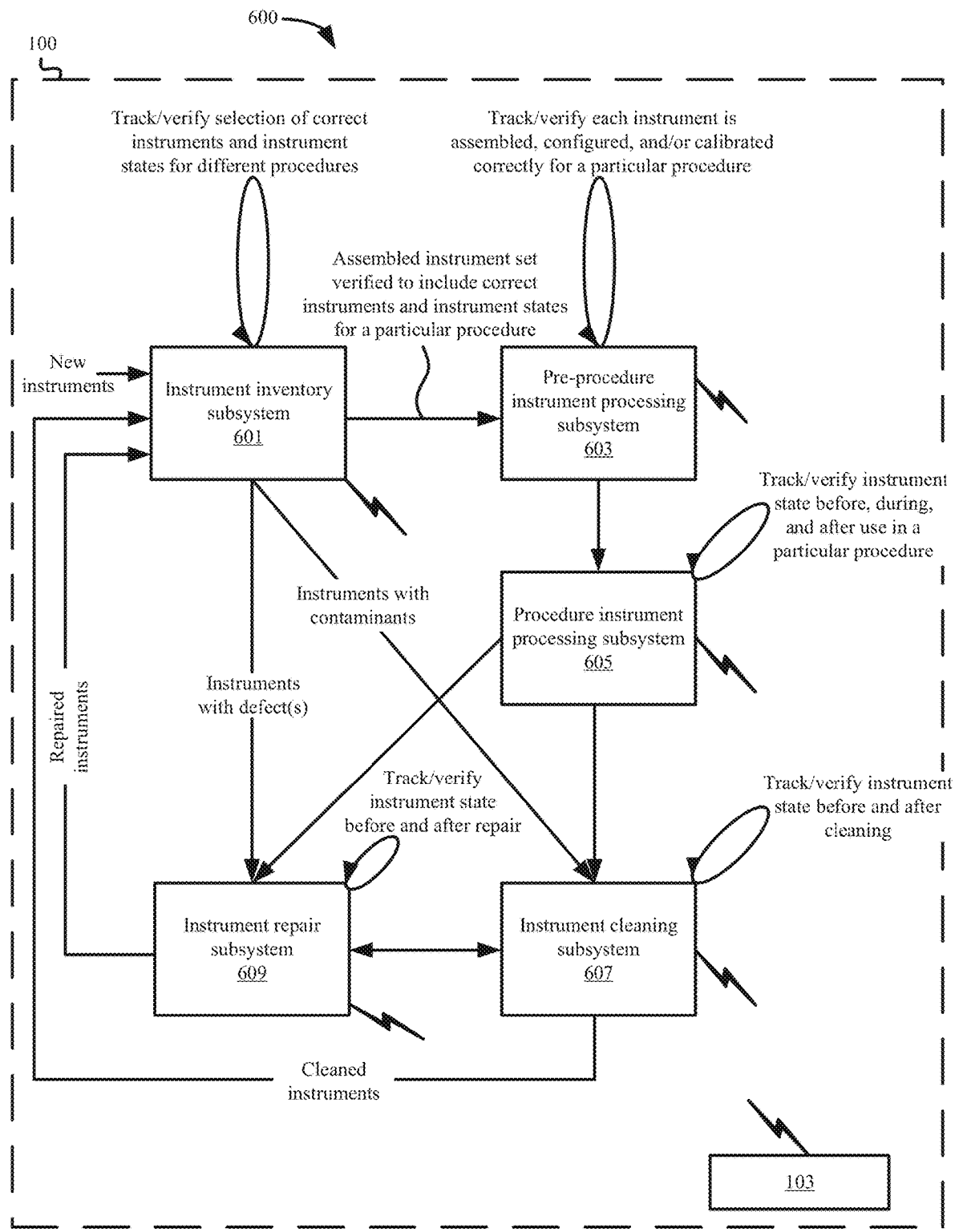
FIG. 6 illustrates a distributed architecture for the inventory control system in accordance with some embodiments presented herein.

FIG. 6 illustrates a distributed architecture 600 for inventory control system 100 in accordance with some embodiments presented herein. As shown in FIG. 6, the distributed architecture 600 for inventory control system 100 may include controller 103, inventory subsystem 601, pre-procedure instrument processing subsystem 603, procedure instrument processing subsystem 605, instrument cleaning subsystem 607, and instrument repair subsystem 609. In some embodiments, the distributed architecture 600 may include more or less subsystems at the same or other stations of a particular site.

Controller 103 may include a centralized device that runs on premises or remotely in the cloud, and that is communicably coupled to subsystems 601, 603, 605, 607, and 609 via one or more wired or wireless networks. In some embodiments, each subsystem 601, 603, 605, 607, and 609 may include portions and/or functionality of controller 103 or, alternatively, each may include a separate instance of controller 103. Moreover, each subsystem 601, 603, 605, 607, and 609 may include one or more sensors for scanning properties of different instruments, one or more robots for manipulating and/or handling the instruments without human intervention, and/or one or more devices for presenting a UI with which inventory control system 100 may communicate with and/or control the actions of different workers. In some embodiments, controller 103 may be communicably coupled to subsystems 601, 603, 605, 607, and 609 at different sites, and may perform the instrument set assembly for each site separately based on sensor data collected from the sensors 101 at 601, 603, 605, 607, and 609 of each site.

Controller 103 may control and/or track the distribution of instruments into and out of storage based on the scanned data from inventory subsystem 601. Inventory subsystem 601 may track new, repaired, and/or cleaned instruments that have been received from subsystems 603, 605, 607, 609, and/or elsewhere and that are available for use in a procedure. Specifically, the sensors of inventory subsystem 601 may scan each new, repaired, and/or cleaned instrument that is delivered to and entered into storage.

The distribution of instruments out of storage may be initiated in response to controller 103 receiving a request to assemble an instrument set for a particular procedure. Controller 103 may use the scanned data from sensors of inventory subsystem 601 to control the distribution of selected instruments out of storage. Specifically, controller 103 may verify selection of a correct instrument with one or more correct states for the requested instrument set and/or the particular procedure based on the scanned data from inventory subsystem 601, and may control and track the distribution of the selected instrument out of inventory subsystem 601 to pre-procedure instrument processing subsystem 603. Similarly, if controller 103 determines, based on the scanned data from inventory subsystem 601, that the state for a selected instrument identifies biological, chemical, and/or other contaminants (e.g., is in need of cleaning) that prevent use of the selected instrument as part of the particular procedure, then controller 103 may control and track the distribution of the selected instrument out of inventory subsystem 601 to instrument cleaning subsystem 607. If controller 103 determines, based on the scanned data from inventory subsystem 601, that the state for a selected instrument identifies one or more defects that prevent use of the selected instrument as part of the particular procedure, then controller 103 may control and track the distribution of the selected instrument out of inventory subsystem 601 to instrument repair subsystem 609.

In some embodiments, inventory subsystem 601 may also be used to manage available inventory and/or the arrangement of instruments in storage. For instance, the sensors of inventory subsystem 601 may detect the manufacturer and type of an instrument and, based upon this determination, may control the placement of the instrument at a known location within the storage and/or inventory. In some embodiments, inventory subsystem 601 may robotically control the placement of the instrument in storage and/or inventory using one or more picking robots of inventory subsystem 601. In some other embodiments, inventory subsystem 601 may direct a worker via associated UIs in the placement of the instrument. Inventory subsystem 601 may be further adapted to include sensors to ensure that the instrument has been placed in the correct storage location, and also to provide an indication when the instrument is removed. In this manner, inventory subsystem 601 may maintain an active count of medical instruments of each manufacture and type. In some embodiments, inventory subsystem 601 may interface with other inventory systems, such as the SPM, CensiTrac, and T-Doc systems.

Controller 103 may use the scanned data from pre-procedure instrument processing subsystem 603 to track instruments that have been transferred for use as part of different medical procedures, and/or to verify instrument assembly, configuration, calibration, and/or other related states that may arise in the procedure room and/or prior the procedure commencing. The sensors of pre-procedure instrument processing subsystem 603 may provide controller 103 with scanned data of an assembled instrument that is assembled from combining, attaching, and/or otherwise installing two or more component instruments in a particular manner, and controller 103 may verify that the assembled instrument is correctly assembled with the correct component instruments. For instance, controller 103 may verify that a drill is assembled with the correct drill bit and/or that a scope is assembled with the correct lens based on the scanned data from pre-procedure instrument processing subsystem 603 and/or AI/ML models for an assembled state of a drill and/or scope for the particular procedure. Similarly, controller 103 may verify that a monitor is configured with the correct settings for a particular procedure and/or patient based on the scanned data from pre-procedure instrument processing subsystem 603 and/or AI/ML models for a properly configured monitor for the particular procedure and/or patient.

Controller 103 may use the scanned data from procedure instrument processing subsystem 605 to track usage of instruments during a particular procedure and/or to verify that the instrument state remains valid for the particular procedure during use and/or after use. For instance, controller 103 may determine that a particular instrument has been contaminated or damaged during a first stage of a procedure based on the scanned data from procedure instrument processing subsystem 605, and may direct the personnel from reusing the particular instrument during a second stage of the procedure. Controller 103 may also control the distribution of instruments after use and/or a completed procedure based on the scanned data from procedure instrument processing subsystem 605. For instance, controller 103 may route a first set of instruments to be sterilized, may route a second set of instruments to be repaired, and/or may route a third set of instruments for disposal or removal from inventory.

Controller 103 may use the scanned data from instrument cleaning subsystem 607 to track instruments and instrument state before and after cleaning and/or sterilization. For instance, scanned data from instrument cleaning subsystem 607 may be used to verify whether instruments previously identified with contaminants have been properly sterilized and/or cleaned prior to being entered back into storage and/or inventory.

Controller 103 may use the scanned data from instrument repair subsystem 609 to track instruments and instrument states before and after maintenance and/or repair. For instance, scanned data from instrument repair subsystem 609 may be used to verify whether instruments previously identified with defects and/or other maintenance issues have been repaired prior to being entered back into storage and/or inventory.

Additionally, inventory control system 100 may use the scanned data from one or more subsystems 601, 603, 605, 607, and 609 to provide additional training data to the AI/ML techniques, and to improve the accuracy of the generated AI/ML models. For instance, scanned data from pre-procedure instrument processing subsystem 603 may include additional examples with which the AI/ML techniques may differentiate between correctly and incorrectly assembled, configured, and/or calibrated instruments, scanned data from procedure instrument processing subsystem 605 and/or instrument cleaning subsystem 607 may include additional examples with which the AI/ML may differentiate between contaminated and cleaned instruments, and/or scanned data from instrument repair subsystem 609 may include additional examples with which the AI/ML may differentiate between instruments with defects and repaired instruments without defects. Improving the modeling accuracy may include adding new characteristics to the models that better differentiate the different instrument states (e.g., clean and unclean states, damaged and undamaged states, usable and unusable states, correctly configured and incorrectly configured states, etc.), removing characteristics from the models that are present in opposite states (e.g., a characteristic determined to identify both a clean and unclean instrument state), and/or adjusting weights attributed to different characteristics of the set of characteristics used in differentiating between different instrument states.

In some embodiments, inventory control system 100 may leverage the scanned data and the tracked instrument state to generate predictive analytics that predict future instrument state. Specifically, inventory control system 100 may record historical states of different instruments from when the instruments were introduced into inventory to when the same instruments were removed from inventory, and may use the historical states to train predictive models.

Training the predictive models may include inputting the historical states for different instruments into one or more neural networks, AI/ML classifiers, and/or deep learning techniques. The one or more neural networks, AI/ML classifiers, and/or deep learning techniques may identify patterns, trends, and/or commonality in the historical states that correspond to times in the instrument lifecycle when different instruments experience different defects and/or require maintenance. Additionally, the techniques may identify patterns, trends, and/or commonality in the historical states that predict the impact on an instrument if it is not maintained, repaired, configured, or calibrated at certain times or in response to certain defects and/or issues.

Predictive models may be generated based on the identified patterns, trends, and/or commonality with probability values that predict the likelihood of various future states for instruments based on the historical past states of those instruments. Accordingly, the predictive models may predict the remaining useful life of an instrument, when the instrument may experience different defects, the progression of defects if left unrepaired, expected costs (e.g., schedules for when and how often an instrument should be examined, maintained, reset, configured, recalibrated, etc. and the costs associated with following or not following the schedules), and/or other future states of the instrument based on that instrument's past historical states.

In some embodiments, inventory control system 100 may integrate the predictive models as part of the instrument distribution control. For instance, inventory control system 100 may control the distribution of a particular instrument based on the current state and predicted future state of that particular instrument.

Figure 7:
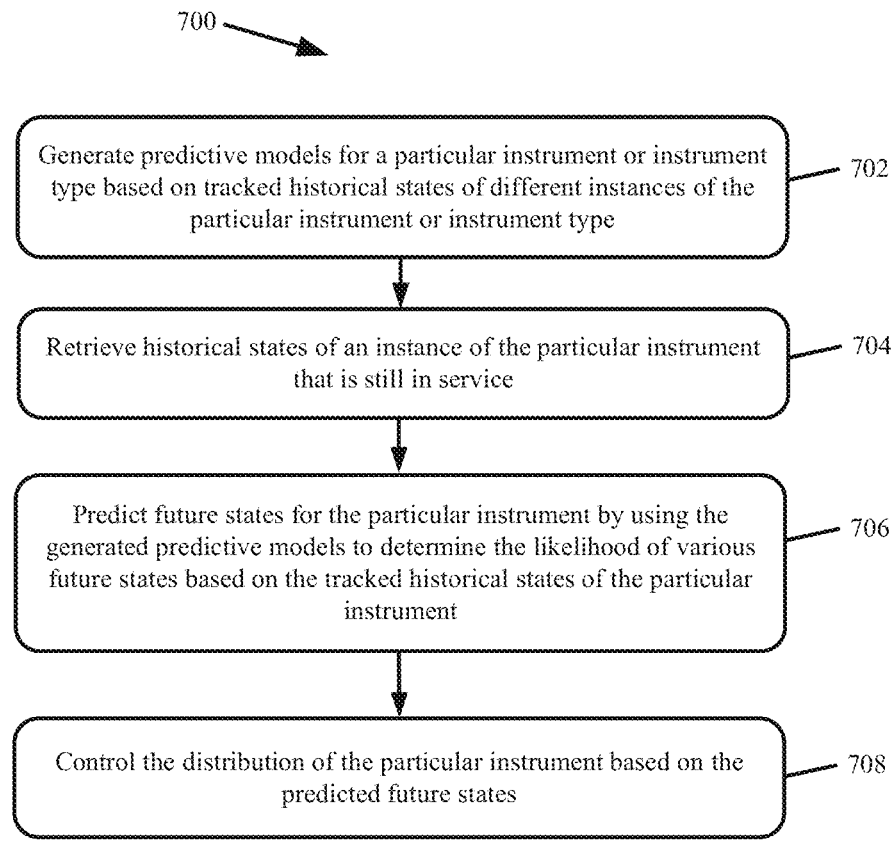
FIG. 7 presents a process for controlling the distribution of instruments based on predictive models and historical instrument state in accordance with some embodiments presented herein.

FIG. 7 presents a process 700 for controlling the distribution of instruments based on predictive models and historical instrument state in accordance with some embodiments presented herein. Process 700 may be implemented by inventory control system 100.

Process 700 may include generating (at 702) predictive models for a particular instrument or instrument type based on tracked historical states of different instances of the particular instrument or instrument type that have since been removed from use (e.g., ended their useful lifespan) and/or have been in use for several years. Generating (at 702) the predictive models may include determining one or more next states that commonly occur for instruments of the same type with the same or similar historic states, and generating probability values for the likelihood that each of the one or more next states occurs whenever the next states are preceded by the same or similar historic states.

In some embodiments, controller 103 may record the instrument state that is output by the AI/ML generated models each time an instrument is scanned by the inventory control system sensors and may associate a timestamp with the instrument state. Controller 103 may record the different instrument states and timestamps to a database record or another data structure that is used to track the historical states of that instrument. The tracked historical states may include the number of times the instrument has been used for different procedures, the number of times the instrument has been repaired, cleaned, and/or otherwise maintained, different maintenance performed on the particular instrument (e.g., different defects that have been repaired, enhancements to the instruments, replaced components, reconditioning, etc.), years in service, and/or other tracked usage associated with that instrument. Accordingly, generating (at 702) the predictive models may include retrieving, analyzing, and/or modeling the historical states recorded in multiple records or data structure for different instances of the same particular instrument or instrument type.

Process 700 may include retrieving (at 704) historical states of an instance of the particular instrument that is still in service and is selected for distribution within the site. For instance, the particular instrument may have been selected as a candidate for inclusion as part of an instrument set for a particular procedure (e.g., the particular instrument is verified as a correct instrument for the particular procedure and the current state of the particular instrument satisfies the state requirements for the particular procedure). The predictive future state modeling of process 700 may be performed for that particular instance of the particular instrument to determine whether or not to retain the particular instrument as part of the instrument set or to distribute the particular instrument elsewhere (e.g., for maintenance, repair, refurbishment, etc.) as a result of predicted future states that may override the distribution of the instrument based on its current state.

Process 700 may include predicting (at 706) future states for the particular instrument by using the generated (at 702) predictive models to determine the likelihood of various future states for the particular instrument based on the tracked historical states of the particular instrument. Predicting (at 706) the future states may include selecting one or more predictive models that have been trained on historical data from other instances of the same particular instrument or instrument type and that have been used for a longer time than the particular instrument and/or that have been retired from service.

Controller 103 may use the UDI or other unique identifier associated with the particular instrument to identify the make and model of the particular instrument and to select the predictive models generated for that instrument make and model. Predicting (at 706) the future states may then include identifying one or more modeled state combinations within the selected predictive models that include the same states or sequence of states as the tracked historical states of the particular instrument, and identifying the one or more output vectors associated with each identified modeled state combinations.

A particular output vector may include probabilities that one or more future states will arise for an instrument with the modeled state combination linked to the particular output vector. For instance, the predictive model may include a modeled state combination for an instrument that is repaired three times for a first set of issues and for an instrument that has been used in 15 or more procedures. The modeled state combination may be linked to an output vector that predicts with a 70% probability that the same instrument will experience a new defect within the next 5 uses that will render the instrument inoperable or will incur a first cost to repair if the instrument is not submitted for specific maintenance or refurbishment, and that predicts with a 90% probability that the same instrument will be defect free for the next 10 uses if the specific maintenance or refurbishment is performed at a second cost that is less than the first cost.

Process 700 may include controlling (at 708) the distribution of the particular instrument based on the predicted future states. For instance, the particular instrument may be verified as a correct instrument with a correct current state for use in a particular procedure. Controlling (at 708) the distribution may include removing the particular instrument from the instrument set of the particular procedure, and routing the particular instrument for the specific maintenance or refurbishment.

The predictive models and the predicted future states may be used to extend the useful life of the instruments by identifying preventative maintenance that may be performed to avoid catastrophic or more serious issues from arising in the future. The predictive models and the predicted future states may be used to reduce costs over an instrument's useful life. Specifically, by identifying issues at early stages or before the issues become more damaging, inventory control system 100 may reduce repair, maintenance, and/or costs associated with the instruments.

In some embodiments, the predictive models and the future state modeling of instruments may be used to issue recalls or to redesign instruments with defective components or designs. In some such embodiments, controller 103 may use the predictive models to identify a high incidence rate of a failure with different units of a particular instrument. Rather than continue usage of working units of the particular instrument until the failure appears, controller 103 may determine that the failure rate associated with a particular issue is greater an allowable threshold, and controller 103 may issue a recall to remove all working units of the particular instrument from use.

Additionally, controller 103 may use the predictive models to identify that the failure results in repairs to a specific component of the particular instrument. Accordingly, the recall may preemptively replace that specific component with a more durable component that does not fail, or may request a redesign of the particular instrument that does not include that specific component that is subject to failure and/or that includes a more durable or better component that reduces the likelihood of the same failure or issue appearing from continued use of the particular instrument.

Figure 8:
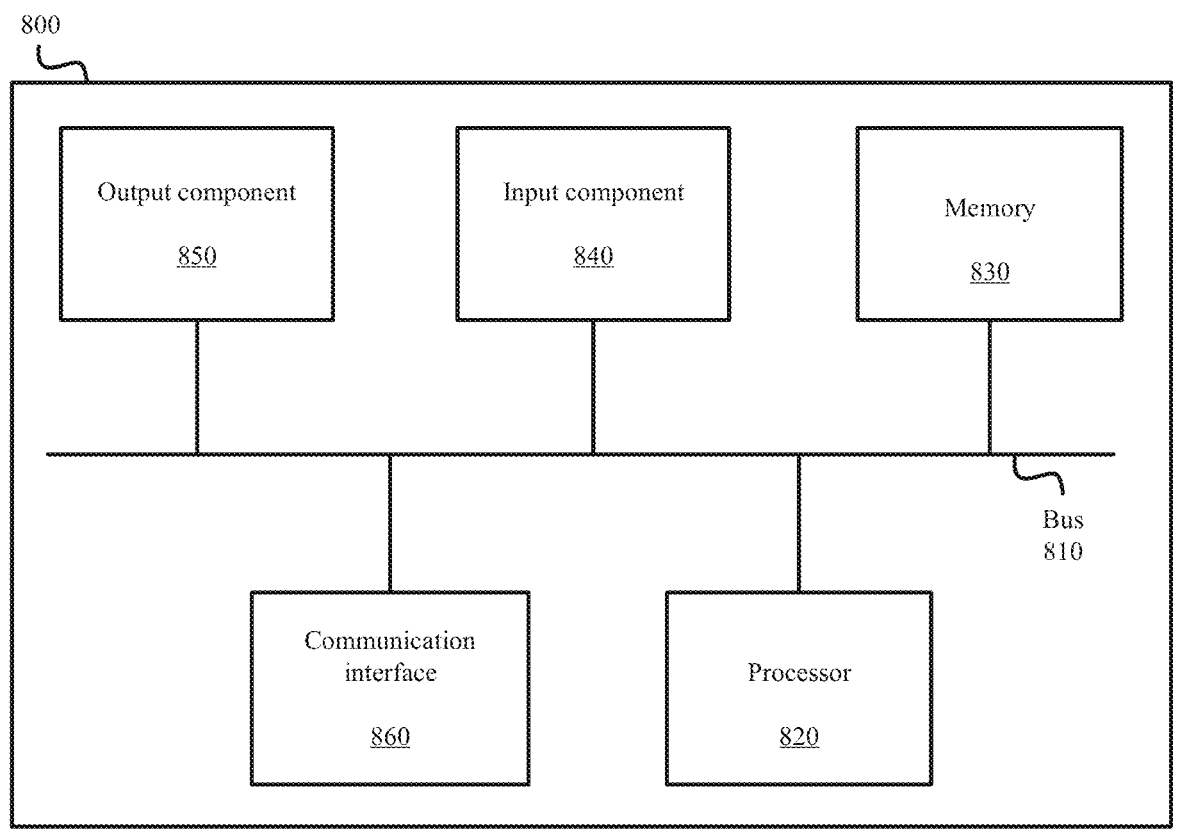
FIG. 8 illustrates example components of one or more devices, according to one or more embodiments described herein.

FIG. 8 is a diagram of example components of device 800. Device 800 may be used to implement one or more of the devices or systems described above (e.g., inventory control system 100, sensors 101, controller 103, UI 105, etc.). Device 800 may include bus 810, processor 820, memory 830, input component 840, output component 850, and communication interface 860. In another implementation, device 800 may include additional, fewer, different, or differently arranged components.

Bus 810 may include one or more communication paths that permit communication among the components of device 800. Processor 820 may include a processor, microprocessor, or processing logic that may interpret and execute instructions. Memory 830 may include any type of dynamic storage device that may store information and instructions for execution by processor 820, and/or any type of non-volatile storage device that may store information for use by processor 820.

Input component 840 may include a mechanism that permits an operator to input information to device 800, such as a keyboard, a keypad, a button, a switch, etc. Output component 850 may include a mechanism that outputs information to the operator, such as a display, a speaker, one or more LEDs, etc.

Communication interface 860 may include any transceiver-like mechanism that enables device 800 to communicate with other devices and/or systems. For example, communication interface 860 may include an Ethernet interface, an optical interface, a coaxial interface, or the like. Communication interface 860 may include a wireless communication device, such as an infrared ("IR") receiver, a Bluetooth® radio, or the like. The wireless communication device may be coupled to an external device, such as a remote control, a wireless keyboard, a mobile telephone, etc. In some embodiments, device 800 may include more than one communication interface 860. For instance, device 800 may include an optical interface and an Ethernet interface.

Device 800 may perform certain operations relating to one or more processes described above. Device 800 may perform these operations in response to processor 820 executing software instructions stored in a computer-readable medium, such as memory 830. A computer-readable medium may be defined as a non-transitory memory device. A memory device may include space within a single physical memory device or spread across multiple physical memory devices. The software instructions may be read into memory 830 from another computer-readable medium or from another device. The software instructions stored in memory 830 may cause processor 820 to perform processes described herein. Alternatively, hardwired circuitry may be used in place of or in combination with software instructions to implement processes described herein. Thus, implementations described herein are not limited to any specific combination of hardware circuitry and software.

The foregoing description of implementations provides illustration and description, but is not intended to be exhaustive or to limit the possible implementations to the precise form disclosed. Modifications and variations are possible in light of the above disclosure or may be acquired from practice of the implementations.

The actual software code or specialized control hardware used to implement an embodiment is not limiting of the embodiment. Thus, the operation and behavior of the embodiment has been described without reference to the specific software code, it being understood that software and control hardware may be designed based on the description herein.

For example, while series of messages, blocks, and/or signals have been described with regard to some of the above figures, the order of the messages, blocks, and/or signals may be modified in other implementations. Further, non-dependent blocks and/or signals may be performed in parallel. Additionally, while the figures have been described in the context of particular devices performing particular acts, in practice, one or more other devices may perform some or all of these acts in lieu of, or in addition to, the above-mentioned devices.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

Further, while certain connections or devices are shown, in practice, additional, fewer, or different, connections or devices may be used. Furthermore, while various devices and networks are shown separately, in practice, the functionality of multiple devices may be performed by a single device, or the functionality of one device may be performed by multiple devices. Further, while some devices are shown as communicating with a network, some such devices may be incorporated, in whole or in part, as a part of the network.

To the extent the aforementioned embodiments collect, store or employ personal information provided by individuals, it should be understood that such information shall be used in accordance with all applicable laws concerning protection of personal information. Additionally, the collection, storage and use of such information may be subject to consent of the individual to such activity, for example, through well-known "opt-in" or "opt-out" processes as may be appropriate for the situation and type of information. Storage and use of personal information may be in an appropriately secure manner reflective of the type of information, for example, through various encryption and anonymization techniques for particularly sensitive information.

Some implementations described herein may be described in conjunction with thresholds. The term "greater than" (or similar terms), as used herein to describe a relationship of a value to a threshold, may be used interchangeably with the term "greater than or equal to" (or similar terms). Similarly, the term "less than" (or similar terms), as used herein to describe a relationship of a value to a threshold, may be used interchangeably with the term "less than or equal to" (or similar terms). As used herein, "exceeding" a threshold (or similar terms) may be used interchangeably with "being greater than a threshold," "being greater than or equal to a threshold," "being less than a threshold," "being less than or equal to a threshold," or other similar terms, depending on the context in which the threshold is used.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items, and may be used interchangeably with the phrase "one or more." Where only one item is intended, the terms "one," "single," "only," or similar language is used. Further, the phrase "based on" is intended to mean "based, at least in part, on" unless explicitly stated otherwise.

What is claimed is:
1. A method comprising:
  receiving a request for two or more instruments with particular states to be assembled as part of an instrument set at a first location;
  presenting, on a display, first identifying information with which to differentiate a first instrument of the instrument set from a plurality of instruments in an available inventory;

scanning one or more states of a first selection from the plurality of instruments using one or more sensors;

updating a state of the instrument set in response to verifying that the one or more states of the first selection represent the first instrument with a first set of states by at least a threshold probability;

presenting, on the display, second identifying information with which to differentiate a second instrument of the instrument set from the plurality of instruments;

scanning one or more states of a second selection from the plurality of instruments using the one or more sensors;

updating the state of the instrument set in response to verifying that the one or more states of the second selection represent the second instrument with a second set of states by at least the threshold probability; and controlling distribution of the instrument set from the first location to a second location in response to determining that the first selection and the second selection complete the instrument set with the particular states for the two or more instruments of the instrument set.

2. The method of claim 1, wherein the plurality of instruments comprises a plurality of equipment and devices used for a plurality of medical procedures, and wherein the instrument set comprises two or more equipment and devices for a particular medical procedure.

3. The method of claim 1,
wherein updating the state of the instrument set in response to verifying that the one or more states of the first selection represent the first instrument with the first set of states by at least the threshold probability comprises detecting placement of the first selection within an assemblage that is created for the instrument set; and
wherein updating the state of the instrument set in response to verifying that the one or more states of the second selection represent the second instrument with the second set of states by at least the threshold probability comprises detecting placement of the second selection within the assemblage using the one or more sensors.

4. The method of claim 1, wherein scanning the one or more states of the first selection comprises:
examining the first selection for biological or chemical contaminants; and
determining a sterilization state of the first selection based on said examining.

5. The method of claim 4, wherein verifying that the one or more states of the first selection represent the first instrument with the first set of states by at least the threshold probability comprises:
verifying that the sterilization state of the first selection satisfies a sterilization state required for using the first instrument in a particular procedure associated with the request in response to the biological or chemical contaminants examined on the first selection being less than biological or chemical contaminants associated with the sterilization state required for using the first instrument in the particular procedure.

6. The method of claim 4, wherein examining the first selection comprises:
detecting the biological or chemical contaminants based on one or more of reflectivity or ultraviolet light image characteristics across the first selection.

7. The method of claim 1, wherein scanning the one or more states of the first selection comprises:
examining the first selection for material defects; and
wherein verifying that the one or more states of the first selection represent the first instrument with the first set of states by at least the threshold probability comprises determining that the first selection is free of material defects that violate a specified condition for the first instrument in the first set of states.

8. The method of claim 1, wherein scanning the one or more states of the first selection comprises:
exposing the first selection to different electromagnetic spectrum wavelengths or frequencies; and
defining the one or more states of the first selection based on a structural composition of the first selection or matter that is detected on the first selection in response to exposing the first selection to the different electromagnetic spectrum wavelengths or frequencies.

9. The method of claim 1, wherein scanning the one or more states of the first selection comprises:
imaging the first selection using one or more lasers, light, sound, or Light Detection and Ranging ("LiDAR"); and
defining the one or more states of the first selection based on a number of defects or contaminants detected from imaging the first selection.

10. The method of claim 1,
wherein scanning the one or more states of the first selection comprises measuring a plurality of properties associated with the first selection; and
wherein verifying that the one or more states of the first selection represent the first instrument with the first set of states by at least the threshold probability comprises determining that the plurality of properties measured for the first selection are within a set of ranges specified for corresponding properties in the first set of states defined for the first instrument.

11. The method of claim 1 further comprising:
obtaining a plurality of scans of multiple units of the first instrument before and after usage in one or more procedures;
determining the first set of states that differentiate the first instrument before usage in the one or more procedures from the first instrument after usage in the one or more procedures based on differences in the plurality of scans; and
generating a model with probability values for a contribution by which each state of the first set of states differentiates the first instrument before usage from the first instrument after usage.

12. The method of claim 1 further comprising:
obtaining a plurality of scans of multiple units of the first instrument with the first set of states corresponding to one or more features, measurements, or properties of the first instrument that meet requirements for one or more uses involving the first instrument, and with a third set of states corresponding to one or more features, measurements, or properties of the first instrument that violate the requirements; and
generating a model that classifies a condition of the first instrument based on the first set of states and the third set of states.

13. The method of claim 1 further comprising:
scanning one or more states of a third selection from the plurality of instruments in response to presenting the first identifying information and before scanning the one or more states of the first selection;
determining that the one or more states of the third selection violate one or more of the first set of states required for the first instrument; and
modifying the display to direct the third selection away from the instrument set.

14. The method of claim 13 further comprising:
controlling distribution of the third selection from the available inventory to a maintenance destination;
tracking maintenance performed on the third selection; and
updating a predicted remaining useful life of the third selection based on said tracking.

15. The method of claim 1 further comprising:
determining that the first selection corresponds to the first instrument based on a first subset of the one or more states of the first selection identifying a make and model of the first instrument; and
determining that the first selection is in a working condition required for the first instrument based on a second subset of the one or more states of the first selection comprising features, measurements, or properties of the first selection that satisfy features, measurements, or properties required for the first instrument in the first set of states.

16. The method of claim 1 further comprising:
updating the display with instructions for attaching the second selection to the first selection to form a combined instrument in response to verifying that the one or more states of the first selection represent the first instrument with the first set of states by at least the threshold probability and verifying that the one or more states of the second selection represent the second instrument with the second set of states by at least the threshold probability.

17. The method of claim 1, wherein verifying that the one or more states of the first selection represent the first instrument with the first set of states by at least the threshold probability comprises:
verifying that the first selection is calibrated according to a specified calibration for using the first instrument as part of a particular procedure.

18. The method of claim 1, wherein scanning the one or more states of the first selection comprises:
imaging the first selection using lasers or different wavelengths of the electromagnetic spectrum; and
determining a sharpness of the first selection based on said imaging.

19. A system comprising:
a display at a first location;
a one or more sensors at the first location; and
a controller comprising one or more processors configured to:
receive a request for two or more instruments with particular states to be assembled as part of an instrument set at the first location;
present, on the display, first identifying information with which to differentiate a first instrument of the instrument set from a plurality of instruments in an available inventory;
scan one or more states of a first selection from the plurality of instruments using the one or more sensors;
update a state of the instrument set in response to verifying that the one or more states of the first selection represent the first instrument with a first set of states by at least a threshold probability;
present, on the display, second identifying information with which to differentiate a second instrument of the instrument set from the plurality of instruments;
scan one or more states of a second selection from the plurality of instruments using the one or more sensors;
update the state of the instrument set in response to verifying that the one or more states of the second selection represent the second instrument with a second set of states by at least the threshold probability; and
control distribution of the instrument set from the first location to a second location in response to determining that the first selection and the second selection complete the instrument set with the particular states for the two or more instruments of the instrument set.

20. A non-transitory computer-readable medium, storing a plurality of processor-executable instructions to:
receive a request for two or more instruments with particular states to be assembled as part of an instrument set at a first location;
present, on a display, first identifying information with which to differentiate a first instrument of the instrument set from a plurality of instruments in an available inventory;
scan one or more states of a first selection from the plurality of instruments using one or more sensors;
update a state of the instrument set in response to verifying that the one or more states of the first selection represent the first instrument with a first set of states by at least a threshold probability;
present, on the display, second identifying information with which to differentiate a second instrument of the instrument set from the plurality of instruments;
scan one or more states of a second selection from the plurality of instruments using the one or more sensors;
update the state of the instrument set in response to verifying that the one or more states of the second selection represent the second instrument with a second set of states by at least the threshold probability; and
control distribution of the instrument set from the first location to a second location in response to determining that the first selection and the second selection complete the instrument set with the particular states for the two or more instruments of the instrument set.

* * * * *